(12) United States Patent
Fredriksson et al.

(10) Patent No.: US 12,201,851 B2
(45) Date of Patent: Jan. 21, 2025

(54) AUTOMATED TREATMENT PLANNING BY DOSE PREDICTION AND ROBUST DOSE MIMICKING

(71) Applicant: RaySearch Laboratories AB (Publ), Stockholm (SE)

(72) Inventors: Albin Fredriksson, Stockholm (SE); Hanna Gruselius, Bromma (SE); Mats Holmstrom, Värmdö (SE); David Andersson, Uppsala (SE)

(73) Assignee: Raysearch Laboratories AB (publ), Stockholm (SE)

( * ) Notice: Subject to any disclaimer, the term of this patent is extended or adjusted under 35 U.S.C. 154(b) by 0 days.

(21) Appl. No.: 18/255,152

(22) PCT Filed: Nov. 18, 2021

(86) PCT No.: PCT/EP2021/082106
§ 371 (c)(1),
(2) Date: May 31, 2023

(87) PCT Pub. No.: WO2022/117353
PCT Pub. Date: Jun. 9, 2022

(65) Prior Publication Data
US 2023/0381539 A1    Nov. 30, 2023

(30) Foreign Application Priority Data
Dec. 1, 2020 (EP) .................................... 20210949

(51) Int. Cl.
*A61N 5/10* (2006.01)

(52) U.S. Cl.
CPC .... *A61N 5/1031* (2013.01); *A61N 2005/1034* (2013.01)

(58) Field of Classification Search
None
See application file for complete search history.

(56) References Cited

U.S. PATENT DOCUMENTS

2010/0104068 A1* 4/2010 Kilby ................... A61N 5/1031
378/65
2013/0303825 A1* 11/2013 Bert ....................... A61N 5/103
600/1

(Continued)

FOREIGN PATENT DOCUMENTS

WO    2017216219 A1    12/2017

OTHER PUBLICATIONS

McIntosh et al., "Fully automated treatment planning for head and neck radiotherapy using a voxel-based dose prediction and dose mimicking method", Physics in Medicine and Biology, Institute of Physics Publishing, Bristol, GB, vol. 62, No. 15, Jul. 6, 2017, pp. 5926-5944.

(Continued)

*Primary Examiner* — Carrie R Dorna
(74) *Attorney, Agent, or Firm* — Noréns Patentbyrå AB (57) ABSTRACT

A method (100) for generating a treatment plan specifying an irradiation of a patient, the method comprising: a dose inference stage (112), including using a model to infer a spatial dose from patient data; a dose mimicking stage (116), including executing a robust optimization process to generate a deliverable treatment plan which is consistent with the inferred spatial dose, wherein the robust optimization considers a plurality of scenarios relating to patient data uncertainty.

19 Claims, 3 Drawing Sheets

(56) References Cited

U.S. PATENT DOCUMENTS

| | | | | |
|---|---|---|---|---|
| 2015/0087879 | A1* | 3/2015 | Nelms | A61N 5/103 600/1 |
| 2016/0082288 | A1* | 3/2016 | Vahala | A61B 5/742 600/411 |
| 2017/0014642 | A1* | 1/2017 | An | A61N 5/1084 |
| 2018/0117357 | A1* | 5/2018 | Fredriksson | A61N 5/1077 |
| 2019/0021684 | A1* | 1/2019 | Ruebel | A61N 5/1082 |
| 2021/0308485 | A1* | 10/2021 | Koponen | G16H 20/40 |

OTHER PUBLICATIONS

International Search Report & Written Opinion, European Patent Office, Feb. 4, 2022, Rijswijk, Netherlands.

An et al., "Robust treatment planning with conditional value at risk chance constraints in intensity-modulated proton therapy", Med. Phys. 44 (1), Jan. 3, 2017.

Fredriksson, A., "Robust optimization in radiation therapy," Advances and Trends in Optimization with Engineering Applications, T. Terlaky, M. F. Anjos and S. Ahmed (eds.), MOS-SIAM Book Series on Optimization, SIAM, Philadelphia, 2017 [ISBN: 978-1-611974-67-6].

"Machine learning automated treatment planning", RaySearch Laboratories AB (publ), Mar. 28, 2019.

White paper 8, "Robust optimization in Raystation", RaySearch Laboratories AB (publ), Apr. 20, 2017.

Office Action issued Feb. 20, 2024 in corresponding Japanese patent application No. 2023-531503, including English translation. (Cited art JP2019517880 is equivalent to WO2017216219A1, which has already been disclosed).

* cited by examiner

AUTOMATED TREATMENT PLANNING BY DOSE PREDICTION AND ROBUST DOSE MIMICKING

TECHNICAL FIELD

The present disclosure relates to the field of automated radiotherapy treatment planning. It relates in particular to a treatment planning method in which an inferential stage is followed by a dose mimicking stage.

BACKGROUND

Machine learning based on historical treatment plans is used in automated radiotherapy treatment planning to infer (or predict) a spatial dose distribution for a novel patient directly from the planning image. For this purpose, a dose prediction model (atlas) is trained for each past patient and stored in a training database, and novel patients are matched to the most relevant atlases. The dose prediction model outputs, in accordance with a dose prescription and dose constraints of targets and organs-at-risk, a spatial dose distribution which specifies the desired dose-per-voxel. Voxel-based dose mimicking, normally with the aid of an optimization engine, then converts the predicted dose distribution into a deliverable treatment plan dose distribution while balancing different dose-volume objectives.

A treatment planning method with these general characteristics is described in C. McIntosh et al., "Fully automated treatment planning for head and neck radiotherapy using a voxel-based dose prediction and dose mimicking method", Phys. Med. Biol., 62 (2017), pp. 5926-5944 [DOI: 10.1088/1361-6560/aa71f8].

The dose prediction model replaces a significant manual effort in the treatment planning process. This is because the dose-volume objectives are typically normally set on the basis of numerous trade-offs between the various dose constraints and the dose prescription. The training of the dose prediction model aims to capture best practices and reap valuable knowhow from the historical cases.

The inventors have observed that the automated treatment planning according to this approach is sometimes more sensitive to poor input data quality than manual planning. Likewise, the available treatment planning techniques have a limited ability to absorb and utilize a concrete expectation of an error which may affect the input data. If the patient's position changes significantly between the imaging and a treatment session, to mention one example, the delivered treatment will not be of optimal quality. Addressing this problem would render the automated treatment planning more attractive and more broadly applicable.

SUMMARY

One objective of the present disclosure is to propose an automated method for generating a treatment plan with an improved robustness to data quality fluctuations, and to patient data uncertainties specifically. It is a further objective to propose such a method which considers and makes allowance for multiple uncertainty scenarios. A still further objective is to make available a treatment planning system with one or more of these characteristics.

These and other objectives are achieved by the invention as defined in the independent claims. The dependent claims relate to advantageous embodiments of the invention.

In a first aspect, a method for generating a treatment plan specifying an irradiation of a patient comprises a dose inference stage followed by a dose mimicking stage. In the dose inference (or dose prediction) stage, a model is used to infer a spatial dose (or per-voxel dose) from patient data. In the dose mimicking stage, a robust optimization process is executed to generate a deliverable treatment plan which is consistent with the inferred spatial dose. The robust optimization considers a plurality of scenarios relating to patient data uncertainties. Optionally, the robust optimization aims to minimize an objective function which includes said plurality of scenarios.

An effect of considering the patient data uncertainty scenarios in the dose mimicking stage is that the resulting treatment plan will be robust to any patient data errors within the given uncertainties. In other words, despite such errors, the dose delivered to the patient stays consistent with the inferred spatial dose and will not risk underdosing the target nor endanger organs-at-risk. A further advantage of the robust optimization approach is that it achieves such effects without inconveniently exposing the patient to a higher total dose than necessary, as is normally the case with straightforward margin-based error handling.

As used herein, a "model" may include a regression model establishing a function from patient data to a suitable spatial dose. In particular it may include a machine-learning model, such as an artificial neural network, a decision tree, a random forest or the like. Training such a machine-learning model may involve applying an input (patient data) and adjusting the weights or other parameters of the model to improve the agreement between the model's output (spatial dose) and a desired output. The desired output may be a manually determined spatial dose, possibly retrieved from historic treatments. A machine-learning model may be referred to as a trainable model.

A "spatial dose" in the sense of this disclosure refers to a radiation dose distribution, by which different doses may be assigned to different patient volumes in an independent manner. The size and configuration of the patient volumes may be chosen to suit the particulars of the treatment planning to be performed. Indeed, the patient volumes, for which the doses are to be defined, may follow anatomical or pathological features of the patient. Alternatively, the patient volumes may be pixels or voxels of a two- or three-dimensional grid (or mesh). The resolution of such a grid may be determined by weighing accuracy against computational complexity; example resolutions are of the order of one centimeter, several millimeters, or one millimeter. The voxels may be cubic (have equal faces) or non-cubic. Accordingly, the spatial dose may specify for each location or each volume of a patient a corresponding dose. The model used in the first aspect serves to infer a spatial dose distribution which specifies the desired dose-per-voxel.

Further, "patient data" as used herein may describe treatment-relevant aspects of the patient's anatomy as well as any extraneous material which is present in the patient's body or its vicinity. To the extent such extraneous material interacts with the radiation to be used (e.g., attenuates, deflects, reflects or even absorbs the radiation), it may need to be accounted for in the course of the treatment planning. Various imaging techniques, including three- or four-dimensional computed tomography (CT), may be important sources of patient data.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

According to some embodiments, the patient data uncertainties may be modeled by one or more uncertainty parameters representing the strength or magnitude of each uncertainty type. The patient data uncertainties may include localized uncertainties, such as a density uncertainty of the patient's body, a range uncertainty of the radiation used; geometrical uncertainties including the patient setup or patient anatomy; and uncertainties relating to the biological effectiveness of the radiation.

In other embodiments, the patient data uncertainties may be modeled as a perturbation of the spatial dose that has been inferred using the model. The patient data uncertainties may further include a perturbation of the radiation penetrability of a patient volume. Each perturbation may correspond to a scenario to be considered by the robust optimization process. As used herein, a "perturbation" is understood as a global error of relatively small magnitude, such as a small translation, rotation or size change affecting the patient geometry, or alternatively a general rescaling of scalar properties of the patient tissues. Compared to localized errors, perturbations are generally characterized by a higher degree of spatial correlation, and this insight may also assist in their rectification.

In still further embodiments, the method further includes a weighting stage, in which an operator may specify the relative importance of meeting the inferred spatial dose in different volumes. The operator may furthermore specify whether the treatment plan dose is allowed to be above or below the spatial dose, or whether the treatment plan dose is to match the spatial dose as closely as possible. The operator may further be given the option of specifying that the dose in a particular volume shall be arbitrary.

In one embodiment, the robust optimization process is such that successive iterations provide a gradually better agreement with the inferred spatial dose.

In a second aspect, the invention provides a treatment planning system configured to generate a treatment plan specifying an irradiation of a patient. To this end, the treatment planning system may comprise an interface configured to receive patient data; a model configured to infer a spatial dose from patient data; processing circuitry configured to execute a robust optimization process to generate a deliverable treatment plan which is consistent with the inferred spatial dose, wherein the robust optimization considers a plurality of scenarios relating to patient data uncertainty.

The invention further relates to a computer program containing instructions for causing a computer, or the treatment planning system in particular, to carry out the above method. The computer program may be stored or distributed on a data carrier. As used herein, a "data carrier" may be a transitory data carrier, such as modulated electromagnetic or optical waves, or a non-transitory data carrier. Non-transitory data carriers include volatile and non-volatile memories, such as permanent and non-permanent storages of magnetic, optical or solid-state type. Still within the scope of "data carrier", such memories may be fixedly mounted or portable.

BRIEF DESCRIPTION OF THE DRAWINGS

Aspects and embodiments are now described, by way of example, with reference to the accompanying drawings, on which.

DETAILED DESCRIPTION

The aspects of the present disclosure will now be described more fully with reference to the accompanying drawings, on which certain embodiments of the invention are shown. These aspects may, however, be embodied in many different forms and should not be construed as limiting; rather, these embodiments are provided by way of example so that this disclosure will be thorough and complete, and to fully convey the scope of all aspects of invention to those skilled in the art. Like numbers refer to like elements throughout the description.

Figure 1:
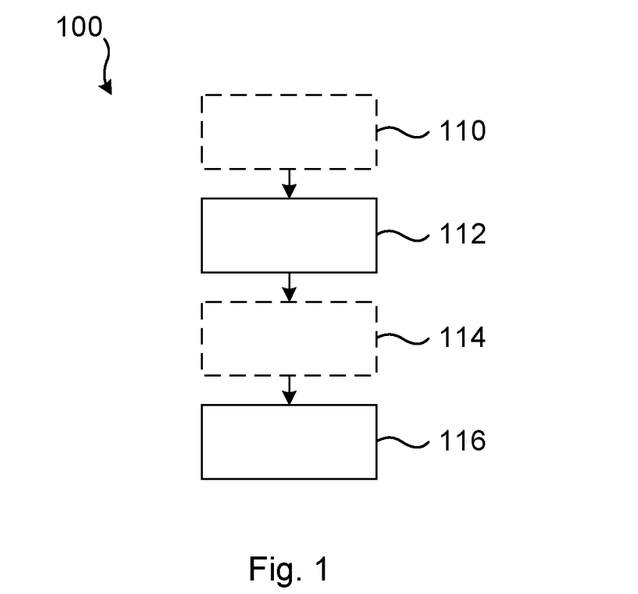
FIG. 1 is a flowchart of a method according to embodiments herein.
Figure 4:
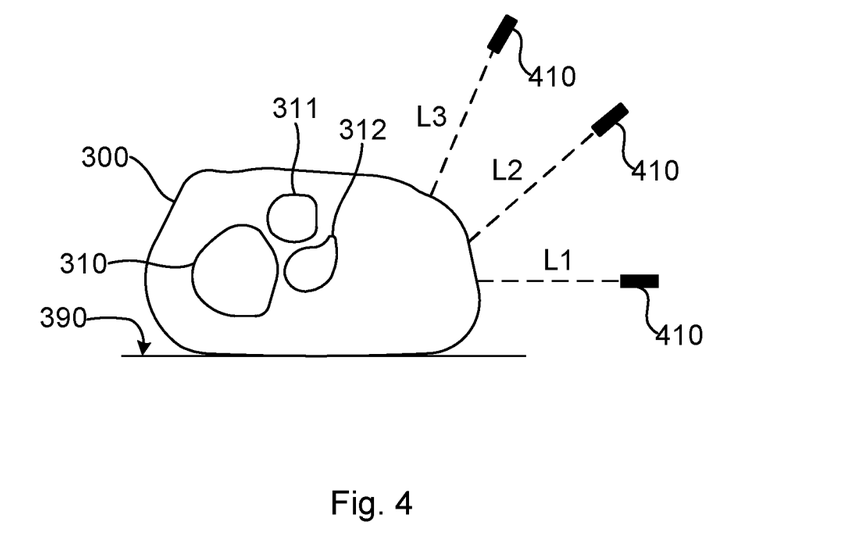
FIG. 4 shows salient parts of a radiation delivery system and a patient in treatment.

FIG. 1 is a flowchart of a method 100 for generating a treatment plan specifying an irradiation of a patient. Such a treatment plan may be executed by a radiation delivery system. Key parts of an example radiation delivery system are illustrated in FIG. 4, which includes at least one radiation source 410. During the treatment, the patient 300 rests on a couch 390 or another support and may be fixed thereto with straps or equivalent means. Rotatory and/or translational relative movement between the radiation source 410 and couch 390 is possible. For example, if a gantry is carrying the radiation source 410, the gantry may be rotatable with respect to one or two axes, and the couch 390 may be rotatable round a vertical axis and translatable in at least one dimension. The use of a gantry makes available a multitude of beam angles (or incidence directions) $L_1$, $L_2$, $L_3$, also outside of the plane of the drawing. The beam angles $L_1$, $L_2$, $L_3$ may be used to deliver a corresponding plurality of spots in ion therapy. The treatment plan may specify fluence and/or particle energy values for all or some of the available spots. It is not uncommon for a treatment plan to engage thousands of spots, and occasionally hundreds of thousands of spots. A photon therapy treatment plan may assign a sequence of settings of a multi-leaf collimator to each of the beam angles $L_1$, $L_2$, $L_3$. In volumetric modulated arc therapy (VMAT), to mention yet another example, the radiation dose is delivered continuously during rotation of the gantry and the while multi-leaf collimator is regulated in accordance with the treatment plan.

The physical radiation dose that will be absorbed in a particular volume of the patient when the treatment plan is carried out may not be explicit from a particular treatment plan; rather relatively complex computations may be required to determine or estimate the physical dose. In addition to the fluence representation already mentioned, a treatment plan may be expressed as a set of machine-executable instructions to be given to a radiation delivery system of the specific type that the treatment planner is going to use. It is to be expected that the radiation delivery system has structural and functional limitations which translate into a limited set of deliverable (or feasible) dose distributions that the system can deliver. Similarly, a dose distribution which is deliverable using a first type of radiation delivery is not necessarily deliverable by a second, different type.

A definition of patient data was given above. Before proceeding to the description of the method 100, it will be helpful to review important classes of patient data uncertainty, which will be discussed with reference to FIG. 3.

Figure 3A:
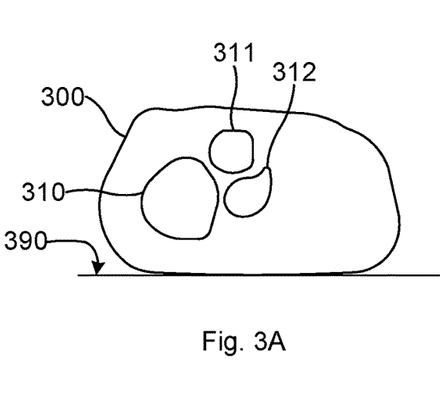
FIG. 3 are cross section views illustrating different types of patient data uncertainties.

FIG. 3A shows the nominal or basic case. It is a transverse section of a patient 300 in a correct setup on a substrate 390, which may be a treatment or imaging couch. Visible in the patient's 300 body are volumes (or more generally regions-of-interest) 310, 311, 312, which are associated with different densities and, for treatment volumes and organs-at-risk, are further associated with desired doses to be delivered. The volumes 310, 311, 312 are shown disjoint although overlaps are not uncommon, also between a treatment volume and an organ-at-risk. It is recalled that the desired doses may be derived from a spatial dose inferred from patient data. A possible reason for delineating also volumes that are not to be associated with doses is that their radiation penetrability differs notably from the surrounding tissue and therefore need to be considered in the treatment planning. The actual situation at treatment time—which in fractionated treatment may be one of multiple spaced—apart times—oftentimes differs from the nominal case. For example, the patient 300 may have undergone organ motion, lost or gained weight, assumed an incorrect pose on the substrate 390, or the densities of the patient volumes 310, 311, 312 may have been measured with errors.

Figure 3B:
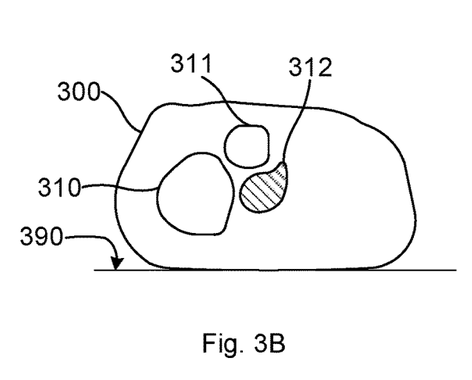

As one example, FIG. 3B shows a scenario with a density error affecting one of the organs 312. The true density of the organ 312 differs quantitatively from the nominal density according to FIG. 3A. In this connection, density may refer to one or more of: image density, radiodensity, mass density, particle stopping power of the volume 312. Further, a range uncertainty of the radiation may be expressed in terms of an overall density error of the patient 300.

This framework may also be utilized to express uncertainties relating to the biological effectiveness of the irradiation, as may be captured by a relative biological effectiveness (RBE) factor. RBE factors described in the literature may be in accordance with one or more phenomenologically based parameterization of a linear energy transfer (LET) model, a local effect model (LEM) or a microdosimetric kinetic model (MKM). A plan goal may be expressed in units of a photon-equivalent dose according to a specified RBE model. An error in RBE may change the physical irradiation required to be delivered to an organ to satisfy this plan goal while leaving the penetrability of the same organ unaffected.

Density and range uncertainties may be quantified numerically as at least one uncertainty parameter which is a percentage of the nominal density or range. In an ensuing treatment planning, the density or range uncertainty may be handled by requiring that all final treatment plans shall be therapeutically acceptable even if an error within the uncertainty is at hand.

Figure 3C:
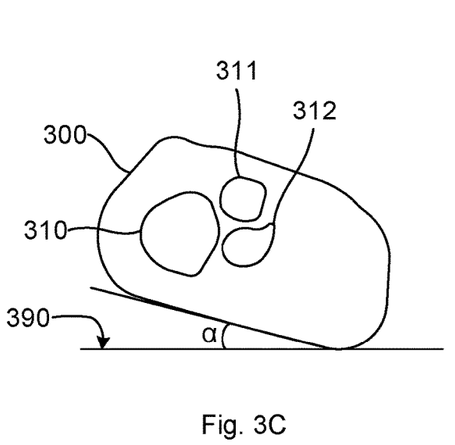

FIG. 3C illustrates a setup error, more precisely, that the patient 300 is resting on the substrate 390 in a position which has been rotated by an angle $\varphi$ (drawn exaggerated for visibility) from the nominal position of FIG. 3A. Here, the densities and relative positions of the volumes 310, 311, 312 remain correct but will agree with the nominal geometry only after an imaginary rotation by an equal angle $\varphi$. The facts are similar if the patient 300 as a whole has been translated a distance $\Delta x$ (not shown) away from its nominal position. Generally speaking, setup errors may include patient position, patient posture and patient orientation. Corresponding uncertainty parameters may represent the maximum errors to take into account in the robust optimization, similar to how a margin is specified for a region-of-interest in conventional planning. The uncertainty parameters may have dimension length, such as right, left, superior, inferior, anterior and posterior position uncertainty in centimeters. For sufficient accuracy, it may be necessary to quantify the setup errors differently for different beams.

Figure 3D:
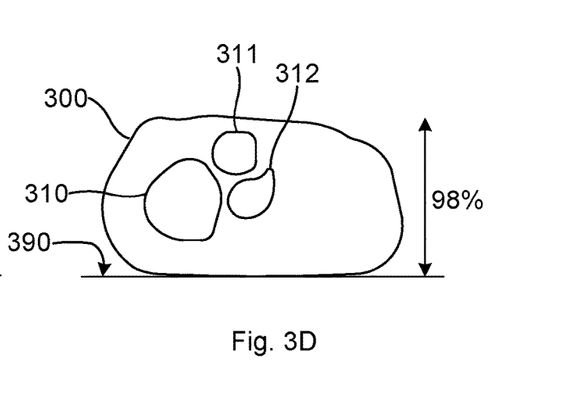
Figure 3E:
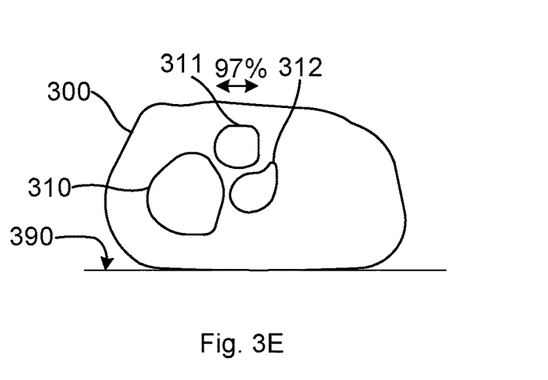

FIG. 3D is a first example of a change in the patient's 300 anatomy as seen in a 2% decrease in anteroposterior diameter from the nominal value. It may relate to a general scale change that includes all organs, thus including volumes 310, 311, 312 as well. Alternatively, the diameter decrease may correspond to a reduction of subcutaneous fat corresponding to a recent weight loss, in which case normally the dimensions of each volume 310, 311, 312 are preserved. According to a second example of an anatomy change, in FIG. 3E, one the volumes 311 has shrunk by 3% while the external patient geometry is substantially unchanged. Such a local size change may for instance be observed as a result of breathing or of a temporary inflation of an organ by gas or liquid at the time of imaging. Uncertainties resulting from anatomy changes may be captured by including additional images of the patient 300, wherein each such additional image may correspond to a scenario to be considered in the treatment planning.

Figure 3F:
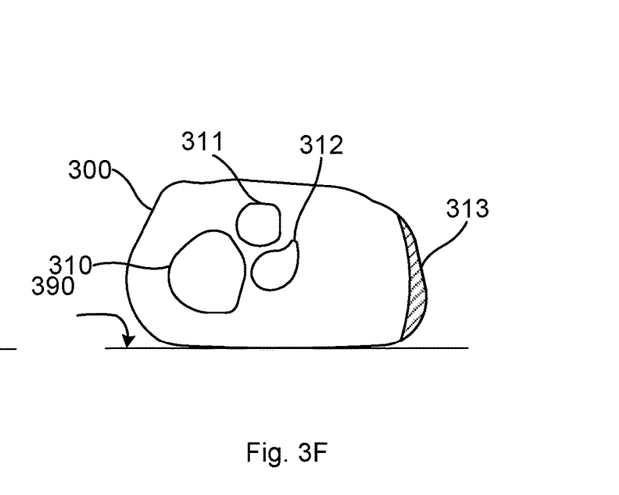

FIG. 3F finally shows that a region 313, which was empty at the time of imaging, has been occupied by extraneous material that may block, absorb, reflect and/or deflect the therapeutic radiation to be delivered. The extraneous material may be clothing, supporting mechanical members (fastening straps) or the like. Considering the effect that the extraneous material may have on radiation beams impinging from the right side may be crucial to the success of the treatment.

For further examples of uncertainty parameters, reference is made to the applicant's white paper "Robust optimization in Raystation", retrievable from https://www.raysearchlabs.com/media/publications/.

According to a basic embodiment, the method 100 according to the flowchart in FIG. 1 comprises a dose inference stage 112 (or dose prediction stage) and a dose mimicking stage 116.

In the dose inference stage 112, a model M is used for generating a spatial dose $\bar{d}(x)$ from patient data F, where $x=(x, y, z)$ is a spatial coordinate vector. The model M may be a regression model, a neural network or any other model within the definition of "model" given above. The training of the model is not a mandatory step of an execution of this method 100 but may have been completed in advance; the model 100 may even utilize a model that was trained by a different party or in collaboration with a that party. For a detailed example of a possible implementation of the inference stage 112, reference is made to section 2.2 of the article by McIntosh et al. mentioned initially, as well as the applicant's white paper "Machine learning. Automated treatment planning", retrievable from https://www.raysearchlabs.com/media/publications/. These references also indicate example source of suitable training data.

In the dose mimicking stage 116, a robust optimization process is utilized to find a treatment plan from a set of deliverable treatment plans. The optimization process may have an iterative structure, in which the successive iterations provide a gradually better agreement with the inferred spatial dose. The optimization process may be pursued until a treatment plan $\pi$ is found which provides a dose $d_\pi(x)$ that (within the numerical precision used, e.g., a multiple of a machine epsilon) best resembles the inferred spatial dose $\bar{d}(x)$. Alternatively, the optimization process is interrupted earlier, when a sufficient degree of agreement has been reached. It is noted that, even if the optimization process is allowed to converge (within the numerical precision) to the plan $\pi$ that provides the dose $d_\pi(x)$ best resembling the inferred spatial dose $\tilde{d}(x)$, it is to be expected that the two doses differ appreciably, as a result of the robust optimization, i.e., the fact that the $d_\pi(x)$ must be acceptable for any of the scenarios considered.

The dose mimicking stage 116 pursues, as one of its plan goals, the agreement with the inferred spatial dose $\tilde{d}(x)$. It is noted that such agreement does not necessarily refer to equality or near-equality, nor at all spatial points. Rather, different embodiments may allow an operator to configure the optimization process such that it tends to satisfy an inequality $$\tilde{d}(x) \leq d_\pi(x), x \in \Omega_1,$$

or $$\tilde{d}(x) \geq d_\pi(x), x \in \Omega_2,$$

(lower bound, upper bound, respectively) between the inferred spatial dose and the treatment plan dose in some volumes $\Omega_1$, $\Omega_2$ and/or an equality $$\tilde{d}(x) = d_\pi(x), x \in \Omega_3,$$

between the inferred spatial dose and the treatment plan dose in further volumes $\Omega_3$ and/or will disregard the treatment plan dose in still further volumes. For example, it may be considered acceptable and even advantageous for the treatment plan dose to exceed the inferred spatial dose in a target volume. Similarly, it may be considered acceptable or advantageous that the treatment plan dose is less than the inferred spatial dose in an organ-at-risk. The radiation delivered to objects and spaces outside the patient's body is typically of no significance and should not constrain the optimization. The agreement with the inferred spatial dose may furthermore be formulated in terms of collective measures, such as dose-volume histograms, dose-at-volume, volume-at-dose and the like. For example, the optimization could be configured such that it aims to render a histogram of the inferred spatial dose as similar as possible to an analogously defined histogram of the treatment plan dose.

In still further embodiments, the optimization process may be configured in such manner that it prioritizes the treatment plan dose's agreement with the inferred spatial dose in some volumes over its agreement with the inferred dose in other volumes. The operator may communicate their preferences in this regard by assigning different weighting $\beta_1$, $\beta_2$, $\beta_3$, ... to the different volumes $\Omega_1$, $\Omega_2$, $\Omega_3$, .... For instance, a weighting factor $\beta_1$ assigned to a first volume can be assigned independently of the weighting factor $\beta_2$ assigned to a second volume. A practical usage of this configurability is to assign the weighting factors to volumes corresponding to different organs-at-risk in an inverse relationship with the biological sensitivity of these organs. The weighting factors may be understood as penalty weights in an objective function of the optimization process. In one embodiment, the weighting factors can be specified at voxel resolution, for example:

$$\beta = \beta(X, Y, Z),$$

where X, Y, Z are discretized spatial coordinates. This resolution has the same level of detail as the treatment plan dose.

Figure 5:
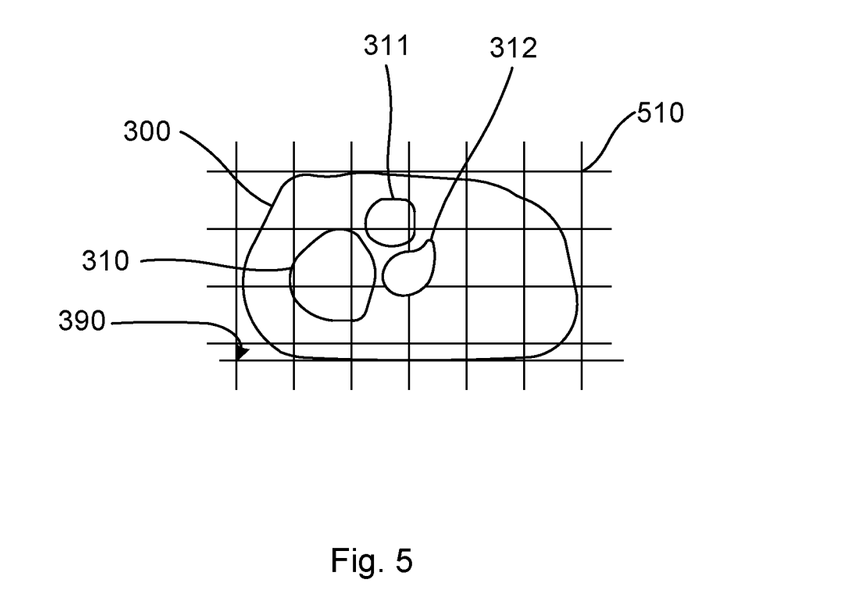
FIG. 5 is a cross section of an example voxel grid.

An example voxel grid 510 is illustrated in FIG. 5, which is a section (transverse section of the patient's body) showing only two dimensions. It is understood that the voxel grid 510 extends into the plane of the drawing (in the patient's longitudinal direction) with an equal or different resolution. Each voxel is addressable by the triple of its discretized coordinates relative to an origin (0,0,0).

The robust optimization process in the step 116 may include solving—analytically or numerically—a robust optimization problem, in which the objective function or a constraint, or both, include an undefined parameter which is allowed to vary over a specified, finite or infinite range. Even though an optimization problem with these characteristics can be likened to a 'moving target', both analytic and numerical methods for addressing important classes of such problems have been developed, along with a body of theoretical results.

A robust optimization problem may be formulated probabilistically or deterministically. Maximin and minimax problems are two deterministic formulations that have proven useful for treatment planning in cases where patient data errors are quantified by uncertainty parameters u, v, w, .... The parameters may be defined in respective ranges $I_u$, $I_v$, $I_w$, ... and represent length, mass, concentration or various dimensionless quantities. The ranges may be based on measurements on a patient population and protocols. An aim of such measurements may be to estimate the probability distribution of each uncertainty parameter, whereby the confidence level that results from optimizing over a tentative set of ranges can be computed as a multidimensional integral in a per se well-known manner.

The set of uncertainty parameters to be used in an execution of the method 100 may be configured by an operator in a preceding step 110. The operator may further be given the option of accepting pre-configured deault ranges that provide a desired confidence level. The default ranges may be specific to a particular cancer type or bodily region. As an example, the recommended setup uncertainty is 0.4 cm and the density uncertainty is 3% in prostate cancer treatment. The default ranges may be equal to uncertainty ranges that were used in training the model, from which the spatial dose is inferred in step 112. Alternatively, the operator specifies the respective ranges manually.

In a simple example with one-dimensional uncertainty on the objective function, a possible minimax formulation reads as follows:

$$\min_{a \in A} \max_{u \in I_u} f(a; u)$$

$$\text{subject to } g_j(a) \leq 0, j \in J$$

$$h_k(a) = 0, k \in K.$$

Here, A is the set of feasible plan parameters in the sense that each element $a \in A$ determines a treatment plan $\pi(a)$. Each of the constraint index sets J, K may be populated or empty. The uncertainty range may be a function of the optimization variable a, that is, $I_u = I_u(a)$.

Alternatively or additionally, the uncertainty may affect the constraints of the problem. Various techniques exist for converting a constraint into a term in the objective function; such a term may be a barrier function or indicator function assigning a penalty to such a values which violate the constraint. There are also ways to translate a component of the objective function into one or more constraints, including linearization techniques and preconditioning techniques.

As another example, the objective function is treated as a stochastic function which depends on the uncertainty u, wherein the expected value is optimized:

$$\min_{a \in A} \mathbb{E}_u[f(a; u)].$$

Further still, the treatment plan may be derived by optimizing the so-called voxel-wise worst case of the dose distribution. For each voxel x, the optimization process is designed to approach the maximum dose (taken over $I_u$) to the inferred spatial dose $\tilde{d}(x)$ and, concurrently, to approach the minimum dose (taken over $I_u$) to the inferred spatial dose $\tilde{d}(x)$. This is achieved by defining an objective function that penalizes the respective deviations, and weighting coefficients can be used to regulate the importance of each of the two sub-objectives.

Both in these examples and in further conceivable implementations, the objective function to be minimized (i.e., the maximum $$\max_{u \in I_u} f(a; u),$$

the expected value $\mathbb{E}_u[f(a;u)]$, and the voxel-wise worst-case difference) includes all the considered scenarios relating to patient data uncertainty. This increases the likelihood that the robust optimization process will converge towards a well-defined single treatment plan. The use of a single objective function including all the scenarios, rather than one objection function for each scenario, may also reduce the risk of irreconcilable partial results.

For further details regarding the formulation of the robust optimization problem, reference is made to A. Fredriksson, "Robust optimization in radiation therapy," *Advances and Trends in Optimization with Engineering Applications*, T. Terlaky, M. F. Anjos and S. Ahmed (eds.), MOS-SIAM Book Series on Optimization, SIAM, Philadelphia, 2017 [ISBN: 978-1-611974-67-6].

Multiple uncertainty parameters u, v, w, . . . can be combined into scenarios s, and this brings the optimization problem (disregarding constraints) into the form:

$$\min_{a \in A} \max_{s \in S} f(a; s),$$

where, again, $S = S(a)$ in general. To illustrate the defining of the scenario set $S$, one may discretize each uncertainty range $I_u$ as a vector U of length $N_u$, which fulfils $U(n) \in I_u$ for all $1 \le n \le N_u$ and $I_u = [U(1), U(N_u)]$. The elements of U may have a linear, logarithmic, random or another suitable spacing within $I_u$. The scenario space for uncertainty parameters u, v, w is obtained as the set $S = \{U(0), U(1), \ldots, U(N_u)\} \times \{V(0), V(1), \ldots, V(N_v)\} \times \{W(0), W(1), \ldots, W(N_w)\}$ of cardinality $N_u N_v N_w$, where x denotes cartesian product of discrete sets.

Another option is to generate the scenarios $S$ by sampling, or joint sampling in particular. For example, setup errors u, v, w in respective spatial dimensions and a range uncertainty q in per cent may be randomly sampled as points inside the hypersphere $u^2+v^2+w^2+q^2=\alpha_{4D}^2$, where $\alpha_{4D}$ is chosen to yield the desired confidence level. This embodiment is an example of $L^2$-constrained joint sampling. In other embodiments, the sampling may be constrained inside an $L^p$ sphere for arbitrary $p \ge 0$. The relative importance of setup errors compared to range errors may be adjusted by substituting a rescaled range error variable $q \mapsto q'=q/\gamma$ for some $\gamma > 0$.

The scenarios $S$ can furthermore by generated by Monte-Carlo sampling. For this purpose, probability distributions of the uncertainty parameters are assumed. In this connection, an assumed probability distribution may be an estimate based on data from a patient population.

Conceptually, the effect of a scenario $s \in S$ may be modeled as a transformation of the inferred spatial dose $\tilde{d}(x)$ into $\tilde{d}_s(x)$, wherein $\tilde{d}(x)$ denotes the dose inferred from the model M as being suitable for the patient data F in the nominal case (cf. FIG. 3A), and $\tilde{d}_s(x)$ denotes the dose of a treatment plan suitable for the patient data $F_s$ according to scenario s. Because the optimization runs over all the defined $s \in S$, the optimization process will tend towards a solution that is suitable regardless of the true patient data.

The transformed dose $\tilde{d}_s(x)$ may be obtained by processing the (nominal) inferred spatial dose $\tilde{d}(x)$. The effect of such transformation may be local (e.g., in case of a local density error) or global (e.g., in case of a rotatory patient setup error). Alternatively, the inference may be repeated once for each scenario s. If the inference from nominal patient data is written $$M: F \mapsto \tilde{d}(x)$$

then the scenario-transformed spatial dose becomes $$M: F_s \mapsto \tilde{d}_s(x), s \in S,$$

It is emphasized that the model M is scenario-independent but is fed with scenario-transformed patient data $F_s$.

An objective function $f_1$ which penalizes non-equality of a treatment plan dose $d_\pi$ and the inferred spatial dose $\tilde{d}$ in a volume $\Omega$ may for example have the following form:

$$f_1(a) = \int_\Omega |d_{\pi(a)}(x) - \tilde{d}(x)|^2 dx$$

or more generally:

$$f_1(a) = \int_\Omega |d_{\pi(a)}(x) - \tilde{d}(x)|^p dx$$

for some exponent $p \ge 0$. In a robust formulation, the effect of the variability across scenarios s may be captured by $$f_1(a; s) = \int_\Omega |d_{\pi(a)}(x) - \tilde{d}_s(x)|^p dx, s \in S.$$

Similarly, if the inferred spatial dose is to act as an upper bound in a volume $\Omega$, the following objective function may be employed:

$$f_2(a; s) = \int_\Omega (d_{\pi(a)}(x) - \tilde{d}_s(x))_+ dx, s \in S.$$

where $(\bullet)_+$ denotes positive part. The function $f_2$ assigns no penalty for such points x where $d_{\pi(a)}(x) \le \tilde{d}_s(x)$. Further, a lower bound may be captured by an objective function on the form $$f_3(a; s) = \int_\Omega (d_{\pi(a)}(x) - \tilde{d}_s(x))_- dx, s \in S.$$

where $(\bullet)_-$ denotes negative part. The positive and negative parts may optionally be raised to a power $p \ge 0$. Each of the above integrals $\int_\Omega \cdot dx$ may be executed as a sum over the voxels located inside $\Omega$.

The objective function may further be formulated in terms of a collective dose measure, such as a cumulative or differential dose-volume histogram, or a volume-at-dose. The volume-at-dose t of a spatial dose d (x) defined in a volume $\Omega$ may be understood as the measure of that portion of $\Omega$ where the dose is greater than or equal to t. With normalization, it may be expressed as follows:

$$VaD(t; d, \Omega) = \frac{|\{\omega \subset \Omega: d(x) \geq t, \forall x \in \omega\}|}{|\Omega|}$$

where |·| denotes measure. It is understood that VaD is generally a left-continuous non-negative function of t satisfying VaD (0; d, $\Omega$)=1 and VaD(t; d, $\Omega$)→0 as t→∞. The following objective function penalizes any (positive or negative) deviation between the volume-at-dose of the treatment dose, denoted VaD (t; $d_{\pi(a)}$, $\Omega$) and the volume-at-dose of the inferred spatial dose under scenario s∈ $\mathcal{S}$, VaD (t; $\tilde{d}_s$, $\Omega$):

$$f_4(a; s) = \int_0^\infty |VaD(t; d_{\pi(a)}, \Omega) - VaD(t; \tilde{d}_s, \Omega)| dt.$$

If only deviations in a specific dose range $[t_1, t_2] \subset [0, \infty)$ are deemed to be a concern, the integration limits may be replaced accordingly. If only a positive deviation is to be penalized, i.e. when the volume-at-dose of the treatment plan dose exceeds the volume-at-dose of the inferred spatial dose, the following objective function may be utilized:

$$f_5(a; s) = \int_0^\infty (VaD(t; d_{\pi(a)}, \Omega) - VaD(t; \tilde{d}_s, \Omega))_+^p dt, \ p \geq 0.$$

Finally, if only a negative deviation is to be penalized, i.e. when the volume-at-dose of the treatment plan dose is less than the volume-at-dose of the inferred spatial dose, one may apply:

$$f_6(a; s) = \int_0^\infty (VaD(t; d_{\pi(a)}, \Omega) - VaD(t; \tilde{d}_s, \Omega))_-^p dt, \ p \geq 0.$$

The integration can be restricted to a smaller dose interval $[t_1, t_2]$ if desired. The volumes $\Omega$ referred to above may be the entire irradiated volume or a sub-volume, such as an organ-at-risk or a treatment volume.

Alternatively or additionally, the effect of a scenario s may be to perturb the radiation penetrability of a subvolume of the patient. Although this perturbation is, in one sense, a change in the patient data, it may primarily affect the calculation of the dose of each treatment plan $\pi(a)$ as a result of attenuation, absorption and the like. Regardless of the physical causes for such dose calculation change, a dependence on the scenario s may be included in the treatment plan dose function, namely, $d_{\pi(a)}(x; s)$. Substituting this term into the objective function $f_1$ provides:

$$f_{1a}(a; s) = \int_\Omega |d_{\pi(a)}(x; s) - \tilde{d}_s(x)|^p dx, \ s \in \mathcal{S}.$$

If the solution of the optimization problem is only required to be robust with respect to the radiation penetrability (i.e., two scenarios in $\mathcal{S}$ differ only with respect to radiation penetrability), then the following objective function may be utilized:

$$f_{1b}(a; s) = \int_\Omega |d_{\pi(a)}(x; s) - \tilde{d}_s(x)|^p dx, \ s \in \mathcal{S}.$$

As the notation indicates, $\tilde{d}(x)$ is independent of s. The further example objective functions $f_2, f_3, f_4, \ldots$ may be modified analogously.

In an important special case, the treatment plan dose is a linear function of the optimization variable a∈ A, that is, $$d_{\pi(a)}(x) = Da,$$

where d is a vector with as many rows as the number of voxels in the irradiated volume. The linearity holds, for example, when the optimization variable a represents a discretization of the beam fluences into area elements; then, each column of the matrix D is the vector of voxel dose depositions that results when the fluence is set to unity in one of the beam fluence area elements. In intensity-modulated proton therapy (IMPT), such a linear representation corresponds to deliverable machine settings. In photon-based intensity-modulated radiation therapy (IMRT), the beam fluences are indirectly controllable via superposition of multi-leaf collimator shapes, so that the linear representation is obtained by converting the beam fluences into deliverable machine settings. Proton spots is a further example where a linear relationship between the treatment plan dose and the optimization variable holds. When the dose varies linearly with the optimization variable a∈ A in any of these ways, the effects of errors may be introduced by replacing D with a scenario-dependent matrix D(s), namely:

$$d_{\pi(a)}(x; s) = D(s)a.$$

The matrix D(s) may be a linear or nonlinear function of s.

In a weighting stage 114 of the method 100, prior to the dose mimicking stage 116, an operator may be enabled to configure weighting factors (or penalty weights) $\beta_1, \beta_2, \beta_3, \ldots$ relating to the different volumes $\Omega_1, \Omega_2, \Omega_3, \ldots$. This option may be utilized to adjust the relative importance of meeting the inferred spatial dose in the different volumes and, thus, the priorities to be respected by the optimization process. In the objective function representation, the weighting factors correspond to coefficients in a linear combination of sub-functions $f_{\Omega_i}$ supported in respective volumes $\Omega_i$:

$$f(a; s) = \sum_{i \geq 1} \beta_i f_{\Omega_i}(a; s).$$

As a further alternative, two weighting factors $\beta_+, \beta_-$ may be specified at voxel resolution, that is, $\beta_\pm = \beta_\pm(X)$, where $X=(X, Y, Z)$ is a vector of discretized spatial coordinates defined on a set $\Gamma$ which indexes all voxels of the irradiated volume. The weighting factors may be included in an objective function of the following general form:

$$f(a; s) = \sum_{X \in \Gamma} \left[ \beta_+(X)\left(d_{\pi(a)}(X) - \tilde{d}_s(X)\right)_+ + \beta_-(X)\left(d_{\pi(a)}(X) - \tilde{d}_s(X)\right)_- \right].$$

Then, the operator may configure the weighting factors such that $\beta_+$ is non-zero in those voxels where the inferred spatial dose is an upper bound, that $\beta_-$ is non-zero in those voxels where the inferred spatial dose is a lower bound, and that both $\beta_+$ and $\beta_-$ are non-zero in those voxels where an equality or approximate equality is desired. Both $\beta_+$ and $\beta_-$ may be set to zero in voxels where the treatment plan dose is unimportant and should not constrain the optimization.

In the preceding sections, the general form of the robust optimization problem has been described and exemplified together with ways to configure the relative importance of different conditions to be met (e.g., equality, upper/lower bound, arbitrary) in different volumes, and to generate the different scenarios which the solution shall be robust to. The completion of the dose mimicking stage 116 may include utilizing an optimization solver to obtain a numerical solution to the minimax problem $$a = \operatorname*{argmin}_{a \in A} \max_{s \in \mathcal{S}} f(a; s),$$

or another formulation of the robust optimization problem, which determines the sought treatment plan $\pi(a)$. Efficient optimization solvers may apply linear, nonlinear or stochastic programming. In iterative methods, it may be useful to initiate the optimization solver with an approximate solution for the non-robust case, that is, disregarding temporarily the variability in $s \in S$. Reference is made the above-cited work by A. Fredriksson (2017), which reviews several optimization techniques in detail, including distributional robustness via linear programming, probabilistic robustness via second-order cone programming, worst-case robustness via nonlinear programming, voxel-wise worst-case robustness via linear and nonlinear programming.

Figure 2:
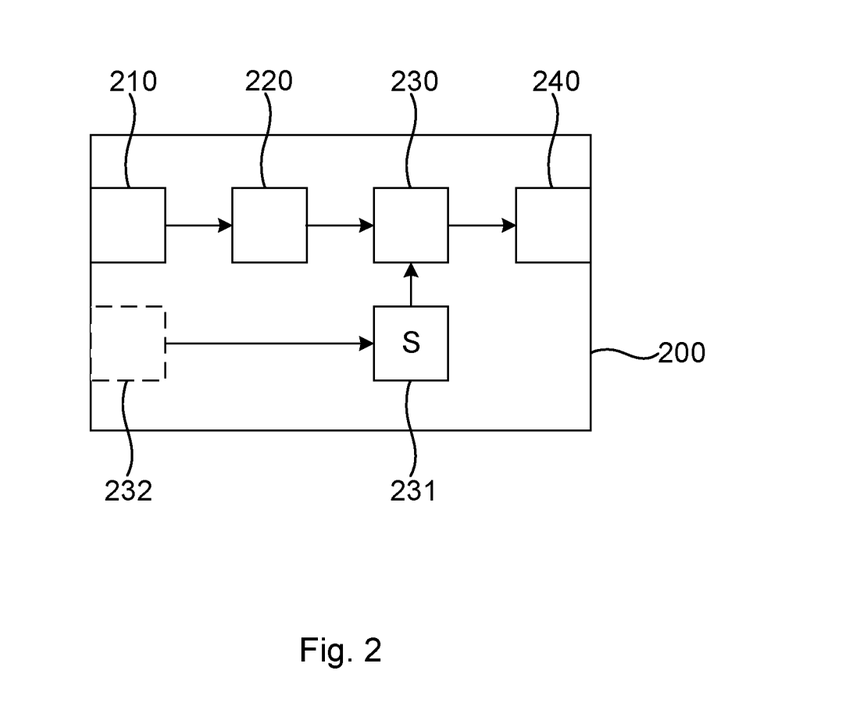
FIG. 2 shows a treatment planning system according to embodiments herein.

The method 100 may be executed by a treatment planning system 200 of the type illustrated in FIG. 2. The treatment planning system 200 may include interfaces 210, 232, 240, memories 220, 231 and processing circuitry 230. A first one of the interfaces 210 may be configured to receive patient data F, from which a spatial dose $\tilde{d}$ is inferred using a trained model M stored in the memory 220. The spatial dose $\tilde{d}$ is forwarded to the processing circuitry 230, which executes an optimization process configured to be robust with respect to a set $S$ of scenarios (or a collection of patient data uncertainties specified in a different format) stored in the memory 231. A second one of the interfaces 232 allows an operator to edit the scenario set $S$. A treatment plan $\pi$ resulting from the optimization process is output via a third one of the interfaces 240. It is understood that the treatment planning system 200 may be implemented by application-specific or programmable processing circuitry, or a combination of both. The logical structure shown in FIG. 2 may not necessarily reflect the physical structure of the system 200.

The aspects of the present disclosure have mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A computer implemented method for generating a treatment plan specifying an irradiation of a patient, the method comprising:
using a model to infer a spatial dose from patient data, the patient data being based on imaging data and describing treatment-relevant aspects of the patient's anatomy and extraneous material present in the patient's body's vicinity;
executing a robust optimization process to generate a deliverable treatment plan which is consistent with the inferred spatial dose, wherein the robust optimization considers a plurality of scenarios relating to patient data uncertainty and successive iterations of the robust optimization process provide a gradually better agreement with the inferred spatial dose; and
outputting the generated treatment plan as a computer readable file to a system configured to deliver radiation to the patient in accordance with the generated treatment plan.

2. The method of claim 1, wherein the plurality of scenarios relating to patient data uncertainty differ with respect to one or more uncertainty parameters representing the patient data uncertainty.

3. The method of claim 2, wherein the one or more uncertainty parameters include one or more of: image density, radiodensity, mass density, particle stopping power of an irradiated volume, and range uncertainty of the radiation.

4. The method of claim 2, wherein the one or more uncertainty parameters include at least one of: patient position, patient posture, patient orientation, and patient setup error.

5. The method of claim 2, wherein the one or more uncertainty parameters include a change in patient anatomy.

6. The method of claim 2, wherein the one or more uncertainty parameters include biological effectiveness of the irradiation.

7. The method of claim 2, wherein there are two or more of the uncertainty parameters with respective ranges and the scenarios correspond to a cartesian product of discretized versions of the ranges.

8. The method of claim 2, wherein the one or more uncertainty parameters include a range error and a setup error, and the scenarios are obtained by an-constrained joint sampling.

9. The method of claim 2, wherein the one or more uncertainty parameters comprises two or more uncertainty parameters and the scenarios are obtained by a Monte-Carlo sampling of the parameters according to assumed probability distributions.

10. The method of claim 2, further comprising an identification of the one or more uncertainty parameters.

11. The method of claim 1, wherein at least one of the scenarios represents a perturbation of the inferred spatial dose.

12. The method of claim 1, wherein at least one of the scenarios represents a perturbation of a radiation penetrability of a subvolume of the patient.

13. The method of claim 1, wherein the optimization process aims to minimize an objective function which penalizes at least one of the following:
the treatment plan dose exceeding the inferred spatial dose in a first volume;
the treatment plan dose being less than the inferred spatial dose in a second volume;
the treatment plan dose deviating from the inferred spatial dose in a third volume.

14. The method of claim 13, wherein the optimization process aims to minimize an objective function which penalizes at least one of the following:
the volume-at-dose of the treatment plan dose, with respect to a fourth volume, exceeding the volume-at-dose of the inferred spatial dose;
the volume-at-dose of the treatment plan dose, with respect to a fifth volume, being less than the volume-at-dose of the inferred spatial dose;
the volume-at-dose of the treatment plan dose, with respect to a sixth volume, deviating from the inferred spatial dose.

15. The method of claim 14, wherein the optimization process aims to minimize an objective function which is independent of a difference between the treatment plan dose and the inferred spatial dose in a seventh volume.

16. The method of claim 15, further comprising defining relative penalty weights relating to some of said first, second, third, fourth, fifth, sixth and seventh volumes.

17. The method of claim 16, further comprising assigning relative penalty weights at voxel resolution.

18. A computer program, stored on a computer readable non-transitory medium and comprising instructions which, when executed by a computer, cause the computer to carry out the method of claim 1.

19. A treatment planning system configured to generate a treatment plan specifying an irradiation of a patient, the system comprising:
an interface configured to receive patient data, the patient data being based on imaging data and describing treatment-relevant aspects of the patient's anatomy and extraneous material present in the patient's body's vicinity;

a model configured to infer a spatial dose from the patient data;

processing circuitry configured to execute a robust optimization process to generate a deliverable treatment plan which is consistent with the inferred spatial dose, wherein the robust optimization considers a plurality of scenarios relating to patient data uncertainty and successive iterations of the robust optimization process provide a gradually better agreement with the inferred spatial dose, and to output the generated treatment plan as a computer readable file; and a system configured to receive the computer readable file and deliver radiation to the patient in accordance with the generated treatment plan.

* * * * *